United States Patent [19]

Berg

[11] Patent Number: 5,417,814

[45] Date of Patent: May 23, 1995

[54] SEPARATION OF 3-METHYL-2-BUTANOL FROM 2-PENTANOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 349,513

[22] Filed: Dec. 5, 1994

[51] Int. Cl.6 .......................... B01D 3/40; C07C 29/84
[52] U.S. Cl. ........................................ 203/60; 203/63; 568/913; 568/918
[58] Field of Search .............. 203/67, 60, 63; 568/913, 918

[56] References Cited

U.S. PATENT DOCUMENTS

| 2,483,246 | 9/1949 | Stribley | 203/60 |
| 2,551,584 | 5/1951 | Carlson et al. | 203/63 |
| 2,552,911 | 5/1951 | Steitz | 203/69 |
| 2,575,243 | 11/1951 | Carlson et al. | 203/60 |
| 2,575,285 | 11/1951 | Carlson et al. | 203/63 |
| 4,670,106 | 6/1987 | Berg et al. | 203/63 |
| 4,969,977 | 11/1990 | Berg | 203/60 |

Primary Examiner—Wilbur Bascomb, Jr.

[57] ABSTRACT

3-Methyl-2-butanol is difficult to separate from 2-pentanol by conventional distillation or rectification because of the proximity of their boiling points. 3-Methyl-2-butanol can be readily separated from 2-pentanol by extractive distillation. Effective agents are acetamide or 2,2,2-trichloroethanol.

1 Claim, No Drawings

SEPARATION OF 3-METHYL-2-BUTANOL FROM 2-PENTANOL BY EXTRACTIVE DISTILLATION

FIELD OF THE INVENTION

This invention relates to a method for separating 3-methyl-2-butanol from 2-pentanol using certain organic liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of oxygenated organic compounds, e.g. the Fischer-Tropech process. In this mixture, a series of homologous alcohols are often produced. Two of the commonest alcohols in this mixture are 3-methyl-2-butanol and 2-pentanol. 3-Methyl-2-butanol boils at 112° C. and 2-pentanol at 118° C. The relative volatility between these two is 1.3 which makes it difficult to separate them by conventional rectification. Extractive distillation would began attractive method of effecting the separation of 3-methyl-2-butanol from 2-pentanol if agents can be found that (1) will create a large apparent relative volatility between 3-methyl-2-butanol and 2-pentanol and (2) are-easy to recover from 2-pentanol. Table 2 shows the relative volatility required to obtain 99% purity. With no agent, the relative volatility is 1.3 and 47 actual plates are required. With an agent giving a relative volatility of 1.4 only 38 plates are required.

TABLE 2

Theoretical and Actual Plates Required vs. Relative Volatility for 3-Methyl-2-butanol-2-Pentanol Separation

| Relative Volatility | Theoretical Plates Required At Total Reflux, 99% Purity | Actual pLtes Required 75% Efficiency |
|---|---|---|
| 1.3 | 35 | 47 |
| 1.4 | 28 | 38 |

OBJECTIVE OF THE INVENTION

The object of this invention is to provide a process or method of extractive distillation that will enhance the relative volatility of 3-methyl-2-butanol from 2-pentanol in their separation in a rectification column. It is a further object of this invention to identify organic compounds which in addition to the above constraints, are stable, can be separated from 2-pentanol and recycled to the extractive column with little decomposition.

SUMMARY OF THE INVENTION

The objects of this invention are provided by a process for separating 3-methyl-2-butanol from 2-pentanol which entails the use of certain organic compounds as the agent in extractive distillation.

DETAILED DESCRIPTION OF THE INVENTION

I have discovered that certain organic compounds will improve the relative volatility of 3-methyl-2-butanol to 2-pentanol and permit the separation of 3-methyl-2-butanol from 2-pentanol by rectification when employed as the agent in extractive distillation. Table 3 lists the compounds that I have found to be effective. They are acetamide and 2,2,2-trichloroethanol.

TABLE 3

Effective Extractive Distillation Agents For Separating 3-Methyl-2-butanol From 2-Pantanol

| Compounds | Relative Volatility |
|---|---|
| None | 1.3 |
| Acetamide | 1.4 |
| 2,2,2-Trichloroethanol | 1.4 |

THE USEFULNESS OF THE INVENTION

The usefulness or utility of this invention can be demonstrated by referring to the data presented in Tables 2 and 3. All of the successful agents show that 3-methyl-2-butanol can be separated from 2-pentanol by means of extractive distillation in a rectification column and that the ease of separation as measured by relative volatility is considerable.

WORKING EXAMPLES

Example 1: Fifteen grams of 3-methyl-2-butanol, fifteen grams of 2-pentanol and 40 grams of acetamide were charged to a vapor-liquid equilibrium still and refluxed for six hours. Analysis indicated a vapor composition of 4S.3% 3-methyl-2-butanol, 51.7% 2-pentanol; a liquid composition of 39.8% 3-methyl-2-butanol, 60.2% 2-pentanol. This is a relative volatility of 1.4.

Example 2: Fifteen grams of 3-methyl-2-butanol, five grams of 2-pentanol and 40 grams of 2,2,2-trichloroethanol were charged to a vapor-liquid equilibrium still and refluxed for three hours. The vapor composition was 75.2% 3-methyl-2-butanol, 24.8% 2-pentanol; the liquid composition was 68.4% 3-methyl-2-butanol, 31.6% 2-pentanol. This is a relative volatility of 1.4.

I claim:

1. A method for recovering 3-methyl-2-butanol from a mixture of 3-methyl-2-butanol and 2-pentanol which comprises distilling a mixture of 3-methyl-2-butanol and 2-pentanol in the presence of about one Dart of an extractive agent per part of 3-methyl-2-butanol - 2-pentanol mixture, recovering the 3-methyl-2-butanol as overhead product and obtaining the 2-pentanol and the extractive agent as bottoms product, wherein said extractive agent consists of acetamide or 2,2,2-trichloroethanol.

* * * * *